(12) United States Patent
Schlecht et al.

(10) Patent No.: US 10,247,682 B2
(45) Date of Patent: Apr. 2, 2019

(54) HELICAL COMPUTED TOMOGRAPHY

(71) Applicant: Illinois Tool Works, Inc., Glenview, IL (US)

(72) Inventors: Joseph Schlecht, Edina, MN (US); Eric Ferley, Rogers, MN (US); Julien Noel, Puteaux (FR)

(73) Assignee: Illinois Tool Works Inc., Glenview, IL (US)

(*) Notice: Subject to any disclaimer, the term of this patent is extended or adjusted under 35 U.S.C. 154(b) by 119 days.

(21) Appl. No.: 14/780,993

(22) PCT Filed: Mar. 31, 2014

(86) PCT No.: PCT/US2014/032422
§ 371 (c)(1),
(2) Date: Sep. 28, 2015

(87) PCT Pub. No.: WO2014/165455
PCT Pub. Date: Oct. 9, 2014

(65) Prior Publication Data
US 2016/0054239 A1    Feb. 25, 2016

Related U.S. Application Data

(60) Provisional application No. 61/808,424, filed on Apr. 4, 2013.

(51) Int. Cl.
*G01N 23/04* (2018.01)
*G01V 5/00* (2006.01)
(Continued)

(52) U.S. Cl.
CPC .......... *G01N 23/046* (2013.01); *A61B 6/032* (2013.01); *A61B 6/52* (2013.01); *G01V 5/005* (2013.01);
(Continued)

(58) Field of Classification Search
CPC ........ G01N 23/046; A61B 6/032; A61B 6/52; A61B 6/5205; G01V 5/005
(Continued)

(56) References Cited

U.S. PATENT DOCUMENTS 4,907,152 A    3/1990  Lempriere
4,969,110 A  * 11/1990  Little ................... G01N 23/046
                                                    348/26

(Continued)

FOREIGN PATENT DOCUMENTS

CN           2935142 Y      8/2007
CN         101071110 A     11/2007
(Continued)

OTHER PUBLICATIONS

Varslot et al., "Fast high-resolution micro-CT with exact reconstruction methods," Developments in X-Ray Tomography VII, Proceedings of SPIE, vol. 7804, Sep. 20, 2010, 10 pp.
(Continued)

*Primary Examiner* — Allen C. Ho
(74) *Attorney, Agent, or Firm* — Shumaker & Sieffert, P.A.

(57) ABSTRACT

An x-ray imaging system may include an x-ray generator, one or more radiation detectors, a rotary stage, a linear translation stage, a motion control system, and a data acquisition system. The rotary stage has an axis of rotation arranged perpendicular to an axis of an x-ray beam emitted by the x-ray generator. The linear translation stage may be configured to move the rotary stage linearly along an axis aligned with the axis of rotation of the rotary stage. The motion control system may synchronize rotational motion of the rotary stage and linear motion of the linear translation stage. The data acquisition system may comprise processors configured to receive user input parameters. The processors
(Continued)

may configure, based at least in part on the user input parameters, the x-ray imaging system to acquire radiographs. The processors may generate a three-dimensional image from the radiographs.

18 Claims, 12 Drawing Sheets

(51) Int. Cl.
    *G01N 23/046*     (2018.01)
    *A61B 6/03*     (2006.01)
    *A61B 6/00*     (2006.01)
    *A61B 6/02*     (2006.01)

(52) U.S. Cl.
    CPC ............ *A61B 6/027* (2013.01); *A61B 6/4085* (2013.01); *A61B 6/5205* (2013.01); *A61B 6/5258* (2013.01); *G01N 2223/1016* (2013.01); *G01N 2223/3307* (2013.01); *G01N 2223/419* (2013.01)

(58) Field of Classification Search
    USPC ............. 378/10, 20, 51, 53, 57, 62, 901, 15; 382/131
    See application file for complete search history.

(56) References Cited

U.S. PATENT DOCUMENTS

| | | | | |
|---|---|---|---|---|
| 4,989,225 A | * | 1/1991 | Gupta | G01N 23/046 378/10 |
| 5,119,408 A | * | 6/1992 | Little | G01N 23/046 378/10 |
| 5,340,988 A | | 8/1994 | Kingsley et al. | |
| 5,878,103 A | * | 3/1999 | Sauer | A61B 6/032 378/15 |
| 5,901,196 A | * | 5/1999 | Sauer | G01N 23/046 378/15 |
| 5,960,055 A | * | 9/1999 | Samarasekera | A61B 6/032 378/4 |
| 5,987,091 A | * | 11/1999 | Miyazaki | G06T 11/005 378/15 |
| 6,041,132 A | * | 3/2000 | Isaacs | G01N 23/046 378/21 |
| 6,104,776 A | * | 8/2000 | Oikawa | G01N 23/06 378/10 |
| 6,327,328 B1 | * | 12/2001 | Satoh | G01N 23/046 378/17 |
| 6,389,101 B1 | * | 5/2002 | Levine | G01N 23/046 378/145 |
| 6,553,094 B1 | * | 4/2003 | Bernardi | G01N 23/046 378/21 |
| 6,574,299 B1 | * | 6/2003 | Katsevich | G06T 11/006 378/15 |
| 6,587,539 B2 | * | 7/2003 | Oikawa | G06T 11/005 378/19 |
| 6,754,299 B2 | * | 6/2004 | Patch | A61B 6/032 378/15 |
| 6,842,502 B2 | * | 1/2005 | Jaffray | A61B 6/032 378/19 |
| 6,909,768 B2 | * | 6/2005 | Takagi | G01N 23/046 378/4 |
| 6,987,270 B2 | * | 1/2006 | Trotter | G01T 1/2985 250/363.03 |
| 7,016,465 B2 | * | 3/2006 | Kamegawa | G01N 23/046 378/19 |
| 7,082,182 B2 | * | 7/2006 | Zhou | A61B 6/032 378/10 |
| 7,127,096 B2 | * | 10/2006 | Kaufman | G06F 19/321 378/207 |
| 7,136,454 B2 | | 11/2006 | Gemdt et al. | |
| 7,177,388 B2 | * | 2/2007 | Takagi | G01N 23/046 378/20 |
| 7,199,357 B1 | | 4/2007 | Oldham et al. | |
| 7,254,211 B2 | * | 8/2007 | Hunt | G01N 23/046 378/20 |
| 7,286,628 B2 | * | 10/2007 | Donnelly | A61B 6/484 378/4 |
| 7,286,630 B2 | * | 10/2007 | Holt | A61B 6/032 378/20 |
| 7,356,115 B2 | * | 4/2008 | Ford | G01N 23/046 378/4 |
| 7,386,090 B2 | * | 6/2008 | Schroeder | A61B 6/032 378/20 |
| 7,394,923 B2 | * | 7/2008 | Zou | G01N 23/046 378/4 |
| 7,450,757 B2 | * | 11/2008 | Kato | G06K 9/00375 382/164 |
| 7,492,862 B2 | * | 2/2009 | Bendahan | G01V 5/0041 378/195 |
| 7,551,714 B2 | * | 6/2009 | Rothschild | G01N 23/046 378/44 |
| 7,570,737 B2 | | 8/2009 | Kang et al. | |
| 7,672,426 B2 | * | 3/2010 | Seppi | G01N 23/046 378/20 |
| 7,714,304 B2 | * | 5/2010 | Poglitsch | G01N 23/046 250/370.09 |
| 7,775,715 B2 | * | 8/2010 | Warner | G01N 23/046 378/20 |
| 7,792,238 B2 | * | 9/2010 | Pack | A61B 6/032 378/4 |
| 7,792,242 B2 | * | 9/2010 | Kamegawa | G01N 23/046 378/20 |
| 7,813,470 B2 | * | 10/2010 | Kuwabara | G01N 23/087 378/4 |
| 7,844,027 B2 | * | 11/2010 | Harding | G01V 5/00 378/20 |
| 7,844,096 B2 | * | 11/2010 | Watson | G06T 11/008 382/131 |
| 7,876,875 B2 | * | 1/2011 | Warner | G01N 23/046 378/10 |
| 7,912,174 B2 | * | 3/2011 | Liu | G01N 23/046 378/10 |
| 7,924,978 B2 | * | 4/2011 | Harding | G01N 23/046 378/84 |
| 7,945,017 B2 | * | 5/2011 | Chen | G01N 23/046 378/57 |
| 7,970,102 B2 | * | 6/2011 | Gilevich | G01V 5/0016 378/57 |
| 7,978,816 B2 | * | 7/2011 | Matsuura | A61B 6/032 378/62 |
| 8,066,102 B2 | * | 11/2011 | Luo | G01N 23/046 187/267 |
| 8,068,579 B1 | * | 11/2011 | Yun | G01N 23/046 378/21 |
| 8,121,247 B2 | * | 2/2012 | Kunzmann | G01N 23/046 378/19 |
| 8,223,916 B2 | * | 7/2012 | Srinivas | A61B 6/025 378/21 |
| 8,229,061 B2 | * | 7/2012 | Hanke | G01N 23/046 378/20 |
| 8,229,413 B2 | | 10/2012 | Vogt et al. | |
| 8,369,483 B2 | * | 2/2013 | Campbell | G01T 1/2018 250/368 |
| 8,422,624 B2 | * | 4/2013 | Christoph | G01B 15/00 378/4 |
| 8,422,626 B2 | * | 4/2013 | Jin | G01N 23/046 378/10 |
| 8,442,353 B2 | * | 5/2013 | Miao | G06T 11/006 358/3.26 |
| 8,478,013 B2 | * | 7/2013 | Nakanishi | G06T 11/005 378/4 |
| 8,538,114 B2 | * | 9/2013 | Yang | G06T 5/002 382/131 |
| 8,542,793 B1 | * | 9/2013 | Jin | G01N 23/046 378/4 |

(56) References Cited

U.S. PATENT DOCUMENTS

| | | | | |
|---|---|---|---|---|
| 8,600,002 B2* | 12/2013 | Hur | A61B 50/37 | 378/21 |
| 8,611,626 B2* | 12/2013 | Miao | G06T 11/005 | 382/131 |
| 8,705,827 B2* | 4/2014 | Zhu | G06T 5/002 | 378/7 |
| 8,804,905 B2* | 8/2014 | Christoph | A61B 6/583 | 378/19 |
| 8,811,570 B2 | 8/2014 | Speller et al. | | |
| 8,938,105 B2* | 1/2015 | Yang | G06T 5/002 | 382/131 |
| 8,953,738 B2* | 2/2015 | Tsuchimoto | G01N 23/046 | 378/4 |
| 8,958,620 B2* | 2/2015 | Dwivedi | A61B 6/469 | 382/131 |
| 8,964,934 B2* | 2/2015 | Ein-Gal | G01N 23/046 | 378/10 |
| 8,971,483 B2* | 3/2015 | Sasaki | G01N 23/046 | 378/16 |
| 8,989,345 B2* | 3/2015 | Kim | G01N 9/24 | 378/207 |
| 9,008,262 B2* | 4/2015 | Nakanishi | A61B 6/032 | 378/19 |
| 9,025,724 B2* | 5/2015 | Lee | G01N 9/24 | 378/10 |
| 9,025,855 B1* | 5/2015 | Christoph | G01N 23/046 | 382/152 |
| 9,036,771 B2* | 5/2015 | Yu | A61B 6/5258 | 378/19 |
| 9,042,510 B2* | 5/2015 | Voland | G01N 23/046 | 378/4 |
| 9,109,998 B2* | 8/2015 | Nathaniel | G01N 23/04 | |
| 9,200,948 B2* | 12/2015 | Jan | A61B 6/035 | |
| 9,291,726 B2* | 3/2016 | Batkilin | G01T 1/2018 | |
| 9,347,894 B2* | 5/2016 | Sims | A61B 5/0035 | |
| 9,459,217 B2* | 10/2016 | Wang | G01N 23/046 | |
| 9,488,605 B2* | 11/2016 | Feser | G01N 23/2206 | |
| 9,495,772 B2* | 11/2016 | Shen | G01T 1/2985 | |
| 9,557,281 B2* | 1/2017 | Badawi | G01N 23/046 | |
| 9,747,706 B2* | 8/2017 | Teshigawara | G06T 11/006 | |
| 9,769,399 B2* | 9/2017 | Bewersdorf | G06T 5/20 | |
| 9,953,414 B2* | 4/2018 | Noda | G06T 7/0012 | |
| 9,980,690 B2* | 5/2018 | Muroi | A61B 6/463 | |
| 10,043,294 B2* | 8/2018 | Fukuda | G06T 11/006 | |
| 2003/0007601 A1 | 1/2003 | Jaffray et al. | | |
| 2009/0207964 A1 | 8/2009 | Pack | | |
| 2010/0303208 A1 | 12/2010 | Baruth et al. | | |
| 2011/0075910 A1 | 3/2011 | Kanagawa et al. | | |
| 2012/0051514 A1 | 3/2012 | Sims et al. | | |
| 2014/0072095 A1 | 3/2014 | Feser et al. | | |
| 2016/0047759 A1 | 2/2016 | Wang et al. | | |

FOREIGN PATENT DOCUMENTS

| | | |
|---|---|---|
| CN | 102667454 A | 9/2012 |
| EP | 1387321 A2 | 2/2004 |
| EP | 2196797 A1 | 6/2010 |
| WO | 03015634 A1 | 2/2003 |
| WO | 2009153789 A1 | 12/2009 |
| WO | 2012147081 A1 | 11/2012 |

OTHER PUBLICATIONS

Tang, et al., "A three-dimensional-weighted cone beam filtered backprojection (CB-FBP) algorithm for image reconstruction in volumetric CT-helical scanning," Institute of Physics Publishing, Phys. Med. Biol. 51, published Jan. 25, 2006; pp. 855-874.

Kalender et al., "Flat-detector computed tomography (FD-CT)," Computer Tomography, Eur Radiol, vol. 17, Springer-Verlag, Jun. 23, 2007, pp. 2767-2779.

Katsevich et al., "Theoretically Exact Filtered Backprojection-Type Inversion Algorithm for Spiral CT," SIAM Journal on Applied Mathematics, vol. 62, No. 6, Jul. 3, 2002, pp. 2012-2026.

Bruandet et al., "Improving x-ray image resolution using subpixel shifts of the detector," SPIE Proceedings, vol. 3661, Medical Imaging 1999: Image Processing, Feb. 20, 1999, 2 pp. (Abstract Only).

International Search Report and Written Opinion of International Application No. PCT/US2014/032422, dated Sep. 29, 2014, 14 pp.

International Preliminary Report on Patentability from International Application No. PCT/U52014/032422, dated Jul. 14, 2015, 7 pp.

Second Written Opinion of International Application No. PCT/US2014/032422, dated Mar. 12, 2015, 6 pp.

Response to Written Opinion dated Sep. 29, 2014, from International Application No. PCT/US2014/032422, dated Feb. 4, 2015, 14 pp.

Response to Second Written Opinion dated Mar. 12, 2015, from International Application No. PCT/US2014/032422, dated May 5, 2015, 3 pp.

Krejci et al., "Enhancement of Spatial Resolution of Roentgenographic Methods Using Deconvolution," 2008 IEEE Nuclear Science Symposium Conference Record, M06-315, Oct. 19-25, 2008, pp. 4124-4129.

Kyrieleis et al., "Image stitching strategies for tomographic imaging of large objects at high resolution at synchrotron sources," Nuclear Instruments and Methods in Physics Research A, vol. 607, Jun. 21, 2009, pp. 677-684.

Thim et al., "Realizing increased sub-pixel spatial resolution in X-ray imaging using displaced multiple images," Nuclear Instruments and Methods in Physics Research A, vol. 633, Jul. 3, 2010, pp. S247-S249.

Wypych et al., "System for Inspection of Large High-Resolution Radiography Datasets," 2011 IEEE Aerospace Conference, Mar. 5-12, 2011, pp. 1-9.

Schön et al., "Dimensionelles Messen mit Helix-Computertomographie," DGZfP-Jahrestagung, Poster 27, 2009, 2 pp. (Applicant points out, in accordance with MPEP 609.04(a), that the year of publication, 2009, is sufficiently earlier than the effective U.S. filing date, Mar. 31, 2014, so that the particular month of publication is not in issue.).

Communication pursuant to Rule 164(2)(b) and Article 94(3) EPC from counterpart European Application No. 14718310.7, dated Jun. 7, 2017, 11 pp.

Dierick, et al., "The use of 2D pixel detectors in micro- and nano-CT applications," Nuclear Instruments & Methods in Physics Research, vol. 591, No. 1, Jun. 11, 2008, pp. 255-259.

Uesugi, et al., "Comparison of lens- and fiber-coupled CCD detetors for X-ray computed tomography," Journal of Synchrotron Radiation, vol. 18, No. 2, Mar. 2011, pp. 217-223.

Dierick, et al., "A LabVIEW based generic CT scanner control software platform," Journal of X-ray Science and Technology, Jan. 2010, 22 pp.

White, et al., "Comparison of fan- and cone-beam imaging capabilities on a portable x-ray imaging system," SPIE—International Society for Optical Engineering Proceedings, vol. 3772, Sep. 22, 1999, pp. 138-146.

Response to Communication pursuant to Article 94(3) EPC dated Jun. 7, 2017, from counterpart European Application No. 14718310.7, filed on Oct. 10, 2017, 4 pp.

* cited by examiner

HELICAL COMPUTED TOMOGRAPHY

This application is a National Stage Entry under 35 U.S.C. § 371 of International Application No. PCT/US2014/032422 filed Mar. 31, 2014, which claims the benefit of U.S. Provisional Application No. 61/808,424, filed Apr. 4, 2013; the entire content of each of which is incorporated herein by reference.

TECHNICAL FIELD

This disclosure relates to computed tomography.

BACKGROUND

X-ray computed tomography (CT) is a procedure that uses computer-processed x-rays to produce tomographic images of an object. A tomographic image of an object is an image of a conceptually two-dimensional "slice" of the object. A computing device may use the tomographic images of the object to generate a 3-dimensional image of the object. X-ray CT may be used for industrial purposes to conduct non-destructive evaluation of objects.

SUMMARY

In general, this disclosure describes an x-ray imaging system for helical (i.e., spiral) computed tomography (CT). The x-ray imaging system includes an x-ray generator, one or more radiation detectors, a rotary stage, a linear translation stage, a motion control system, and a data acquisition system. The x-ray generator may emit a fan-shaped or cone-shaped x-ray beam. The rotary stage has an axis of rotation arranged substantially perpendicular to an axis of the x-ray beam. The linear translation stage is configured to move the rotary stage linearly along an axis aligned with the axis of rotation of the rotary stage. The motion control system synchronizes rotational motion of the rotary stage and linear motion of the linear translation stage such that a point on a sample supported by the rotary stage traces out a spiral or helical pattern. Thus, the rotatory stage may move linearly along an axis while rotating around the same axis. The data acquisition system includes one or more processors configured to receive user input parameters. Based at least in part on the user input parameters, the one or more processors configure the x-ray imaging system to acquire radiographs. The one or more processors generate a three-dimensional image based at least in part on the radiographs.

In one example, this disclosure describes an x-ray imaging system comprising: an x-ray generator; one or more radiation detectors; a rotary stage having an axis of rotation arranged perpendicular to an axis of an x-ray beam emitted by the x-ray generator; a linear translation stage having an axis of movement arranged along the axis of rotation of the rotary stage; a motion control system that synchronizes rotational motion of the rotary stage and linear motion of the linear translation stage such that a point on a sample supported by the rotary stage traces out a spiral or helical pattern; and a data acquisition system comprising one or more processors configured to: receive user input parameters; configure, based at least in part on the user input parameters, the x-ray imaging system to acquire radiographs; and generate a three-dimensional image based at least in part on the radiographs.

In another example, this disclosure describes a method comprising: receiving user input parameters; configuring, based at least in part on the user input parameters, an x-ray imaging system to acquire radiographs, the x-ray imaging system comprising: an x-ray generator; one or more radiation detectors; a rotary stage having an axis of rotation arranged perpendicular to an axis of an x-ray beam emitted by the x-ray generator; a linear translation stage having an axis of movement arranged along the axis of rotation of the rotary stage; and a motion control system that synchronizes rotational motion of the rotary stage and linear motion of the linear translation stage such that a point on a sample supported by the rotary stage traces out a spiral or helical pattern; and generating a three-dimensional image based at least in part on the radiographs.

In another example, this disclosure describes a non-transitory computer-readable data storage medium having instructions stored thereon that, when executed, cause a computing system to: receive user input parameters; configure, based at least in part on the user input parameters, an x-ray imaging system to acquire radiographs, the x-ray imaging system comprising: an x-ray generator; one or more radiation detectors; a rotary stage having an axis of rotation arranged perpendicular to an axis of an x-ray beam emitted by the x-ray generator; a linear translation stage having an axis of movement arranged along the axis of rotation of the rotary stage; and a motion control system that synchronizes rotational motion of the rotary stage and linear motion of the linear translation stage such that a point on a sample supported by the rotary stage traces out a spiral or helical pattern; and generate a three-dimensional image based at least in part on the radiographs.

The details of one or more examples are set forth in the accompanying drawings and the description below. Other features, objects, and advantages will be apparent from the description, drawings, and from the claims.

DETAILED DESCRIPTION

X-ray computed tomography (CT) is a commonly used technique of non-invasively or non-destructively obtaining three-dimensional structures in medical imaging and industrial non-destructive evaluation (NDE). The techniques of this disclosure provide for an apparatus for obtaining the three-dimensional (3D) structure of objects (e.g. elongated objects) using an x-ray CT technique. The techniques of this disclosure also provide for instrumentation, a user control mechanism, and software algorithms of the apparatus. The apparatus may be used for NDE of naturally-occurring objects such as rock core samples, as well as manufactured components and systems. The apparatus may comprise an x-ray generator, a radiation detector, and a rotary stage. The rotary stage may rotate samples so that radiographs can be obtained at different viewing angles. The x-ray generator, the radiation detector, and the rotatory stage may each be mounted on linear positioning stages to place the x-ray generator, the radiation detector, and the rotary stage in different geometric configurations. In one example configuration described in this disclosure, the system may provide a resolution ranging from 0.5 micrometers to 100 micrometers.

Figure 1:
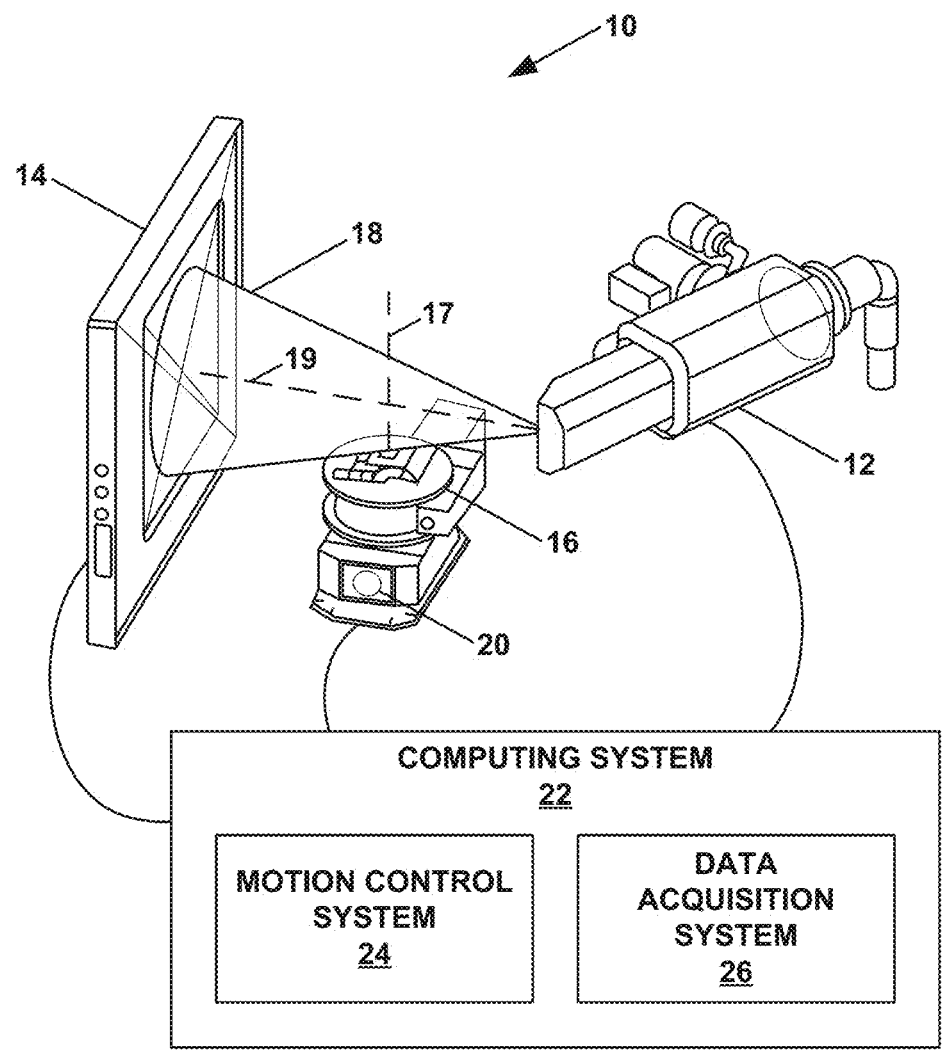
FIG. 1 is a system diagram with both schematic elements and block element, illustrating an example instrumental setup in accordance with one or more examples of this disclosure.

FIG. 1 is a system diagram with both schematic elements and block elements illustrating an example instrumental setup, in accordance with one or more examples of this disclosure. As shown in the example of FIG. 1, an industrial CT system 10 may comprise an x-ray generator 12, a radiation detector 14, and a computing system 22. Although not shown in the example of FIG. 1, industrial CT system 10 may comprise one or more radiation detectors in addition to radiation detector 14.

A sample may be mounted on a rotary stage 16. Example types of samples include machinery, rock cores, or other types of objects. In typical examples, an axis of rotation 17 of rotary stage 16 is perpendicular to the x-ray beam axis 19 (i.e., an axis of an x-ray beam 18 emitted by x-ray generator 12). Accordingly, industrial CT system 10 may acquire radiographs at different projection angles as the sample is rotated in x-ray beam 18. In the example of FIG. 1, x-ray beam 18 is cone-shaped. In other examples, x-ray beam 18 is fan-shaped. In some examples, x-ray generator 12 may provide x-rays with an energy range of 20 keV to 600 keV.

Furthermore, industrial CT system 10 may include a vertical stage 20 that may move vertically. Rotary stage 16 is mounted or otherwise coupled to vertical stage 20 such that rotary stage 16 moves vertically when vertical stage 20 moves vertically. The motion of vertical stage 20 may be synchronized with the rotational motion of rotary stage 16 such that a point on a sample supported by rotary stage 16 and/or vertical stage 20 traces out a spiral or helical pattern. In other examples, rotary stage 16 may be moved linearly in other directions. For instance, industrial CT system 10 may include a stage that moves rotary stage 16 in a direction other than vertical. Accordingly, this disclosure may refer to vertical stage 20 as "linear translation stage 20." In this way, industrial CT system 10 may comprise a linear translation stage 20 having an axis of movement arranged along the axis of rotation 17 of rotary stage 16. Movement of linear translation stage 20 along the axis of rotation 17 of rotary stage 16 results in movement of rotary stage 16 (as well as any sample mounted on rotary stage 16) along the axis of rotation 17 of rotary stage 16.

Radiation detector 14 may comprise a flat panel x-ray detector (FPD) as shown in the example of FIG. 1. In other examples, radiation detector 14 may comprise a lens-coupled scintillation detector, a linear diode array (LDA), or another type of device that detects radiation. Thus, industrial CT system 10 may comprise one or more radiation detectors including at least one of: a flat-panel radiation detector, a lens-coupled high-resolution x-ray detector, and a linear diode array radiation detector.

Furthermore, in the example of FIG. 1, industrial CT system 10 comprises a computing system 22. Computing system 22 may comprise one or more computing devices, such as personal computers, laptop computers, server computers, mainframe computers, special-purpose computers, and so on. In some examples, computing system 22 may be located remotely from other components of industrial CT system 10. For instance, computing system 22 may, from the perspective of users of the other components of industrial CT system 10, exist in "the cloud."

Computing system 22 may implement a motion control system 24 and a computer-controlled data acquisition system 26. Motion control system 24 may synchronize rotational motion of rotary stage 16 and linear motion of linear translation stage 20. In other examples, motion control system 24 may be implemented separately form data acquisition system 24.

Data acquisition system 26 may receive input parameters from one or more users. In some examples, data acquisition system 26 may receive indications (e.g., from input devices, such as keyboards, touchscreens, etc., or remote computing device) of user input of the input parameters. Data acquisition system 26 may configure, based at least in part on the user input parameters, the x-ray imaging system to acquire radiographs. Furthermore, data acquisition system 26 may acquire radiographs from radiation detector 14 (and/or other radiation detectors of industrial CT system 10), digitally record the radiographs, and process the radiographs. For instance, data acquisition system 26 may generate a three-dimensional image based at least in part on the radiographs. In this way, data acquisition system 26 may acquire radiographs, digitally record the radiographs, and reconstruct a 3-dimensional image from the radiographs.

In an example CT cycle, a sample under test may be rotated across a range of 180 degrees with radiographs acquired at specific intervals. The radiographs may then be mathematically assembled into 3D volume data representing the 3D structure of the sample under test. A disadvantage of this type of configuration may be the limited field of view, as only portions of the sample exposed to x-ray beam 18 can be examined. Hence, with elongated samples, only a partial volume can be imaged during each CT cycle. In order to image the complete sample, a series of multiple CT cycles must be performed independently on different portions of the sample, and the resulting series of 3D images must then be stitched numerically to obtain an image of the full structure.

The techniques of this disclosure may overcome this limitation with the use of a motorized linear translation stage 20 with its motion axis parallel to the sample's long axis. During a CT scan, the linear stage (e.g., linear translation stage 20) may continuously move the entire sample across the x-ray beam cone (e.g., x-ray beam 18) in a synchronized fashion to the rotation motion of rotary stage 16. With this additional motion, a point on the sample may effectively trace out a spiral or helical pattern. Hence, this approach may be referred to herein as spiral CT or helical CT. Using this technique, an elongated sample can be scanned in a single cycle without the need of user intervention or additional numerical stitching. The techniques of this disclosure may present significant advantages over the conventional technique for a wide range of applications.

The techniques of this disclosure may apply primarily to industrial CT systems focusing on high-resolution applications. Industrial CT system 10 may include a number of novel elements. For example, industrial CT system 10 may include a novel instrumentation design, including novel detector designs incorporating detectors for a wide range of resolution and field of view combinations. In another example, industrial CT system 10 may use novel numerical algorithms for processing the radiographs and furthermore reconstructing a 3D image from the radiographs.

A flat-panel detector may comprise a layer of scintillation material, such as Cesium Iodide, fabricated on an amorphous silicon on a glass detector array. The scintillator layer may absorb x-rays and may emit visible light photons that are, in turn, detected by a solid state detector. Pixel sizes of radiation detector 14 may range from tens to hundreds of micrometers. For instance, radiation detector 14 may include a flat-panel detector with a pixel size ranging from 25 micrometers to 300 micrometers.

Flat-panel detectors are currently the most commonly used detectors in industrial CT systems in a volumetric CT setup. Flat-panel detectors generally provide 10-100 micrometer resolution in most applications, and fields of view from 10 mm to 400 mm. This design may be well-suited for objects with coarse features such as printed circuit boards and machined or cast components. Higher resolution can be achieved with the use of a lens-coupled detector system that uses lenses with various magnifications to achieve 0.5 micrometer to 10 micrometer resolution and 1 mm to 50 mm fields of view. This design may be well suited for objects with fine feature sizes such as integrated circuit components or cellular structures in biological systems. At the opposite size range, high-energy x-rays of greater than 300 keV may be used to penetrate large objects such as complete assembled machine systems. In these applications, linear diode array detectors are often used to reduce contrast reduction from scattered radiation.

Figure 2:
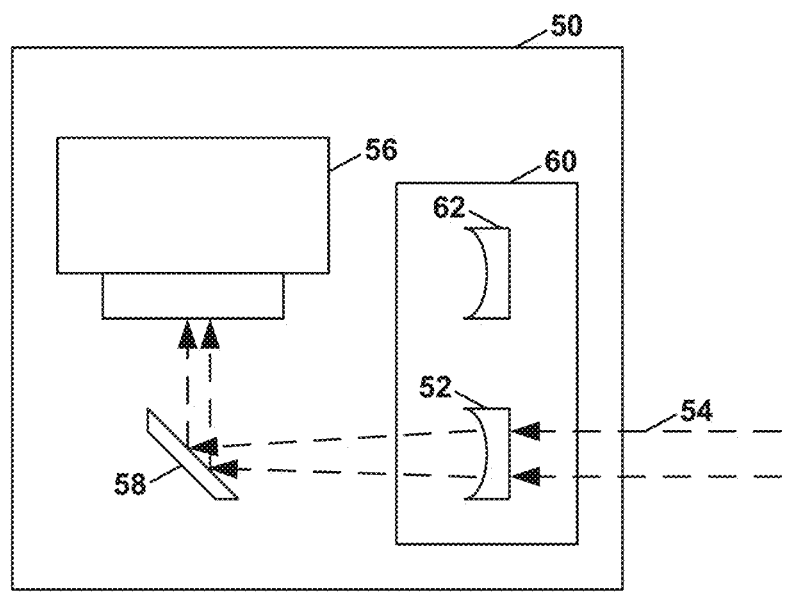
FIG. 2 is a block diagram illustrating an example lens-coupled high-resolution x-ray detector, in accordance with one or more techniques of this disclosure.

FIG. 2 is a block diagram illustrating an example lens-coupled high-resolution x-ray detector 50, in accordance with one or more techniques of this disclosure. Radiation detector 14 of industrial CT system 10 may include lens-coupled high-resolution x-ray detector 50. Lens-coupled high-resolution x-ray detector 50 may use an additional optical lens 52 to relay emitted visible light 54 to a detector 56, such as charge-coupled device (CCD) or complementary metal-oxide-semiconductor (CMOS) detector as shown in the example of FIG. 2. A scintillator layer of radiation detector 14 may emit visible light 54 when the scintillator layer absorbs x-rays emitted by x-ray generator 12 or other x-ray source.

Lens 52 may provide magnification in the range of 0.5× to 100×, thus making the effective pixel size of lens-coupled high-resolution x-ray detector 50 between 0.1 to 20 micrometers. In some examples, lens-coupled high-resolution x-ray detector 50 has a pixel size of 0.1 micrometers to 10 micrometers. In the example of FIG. 2, a mirror 58 directs visible light 54 from lens 52 to detector 56. Furthermore, in the example of FIG. 2, lens 52 is mounted in a rotary turret 60 that includes one or more additional lenses, such as lens 62. Rotary turret 60 may be rotated or otherwise reconfigured such that emitted visible light 54 passes through lens 62 instead of lens 52. Lens 52 and lens 62 may have different focal lengths and hence may be used to achieve different resolutions and/or fields of view. For instance, lens 52 may be a wide-field lens and lens 62 may be a high-resolution lens.

To further mitigate the field of view and resolution limitations of each detector technology (i.e., flat-panel detector technology, lens-coupled high-resolution x-ray detector technology, and LDA technology), industrial CT system 10 of this disclosure may combine two or more of these three types of detector technologies. For example, industrial CT system 10 may comprise a combined flat-panel detector and lens-coupled detector system to produce a multi-scale imaging system capable of both system-scale NDE with complete assemblies as well as detailed examination at a sub-micrometer scale. For instance, industrial CT system 10 may comprise a lens-coupled high-resolution x-ray detector 50 with a pixel size in a range of 0.1 micrometers to 10 micrometers, and a flat-panel detector with a pixel size ranging from 25 micrometers to 300 micrometers. In this example, industrial CT system 10 may include a mechanical mechanism to switch between at least the lens-coupled high-resolution x-ray detector 50 and the flat-panel detector. The use of spiral-CT may further provide extended scanning length with this resolution and field of view combination for elongated objects, such as full rock core samples or missiles.

Figure 3A:
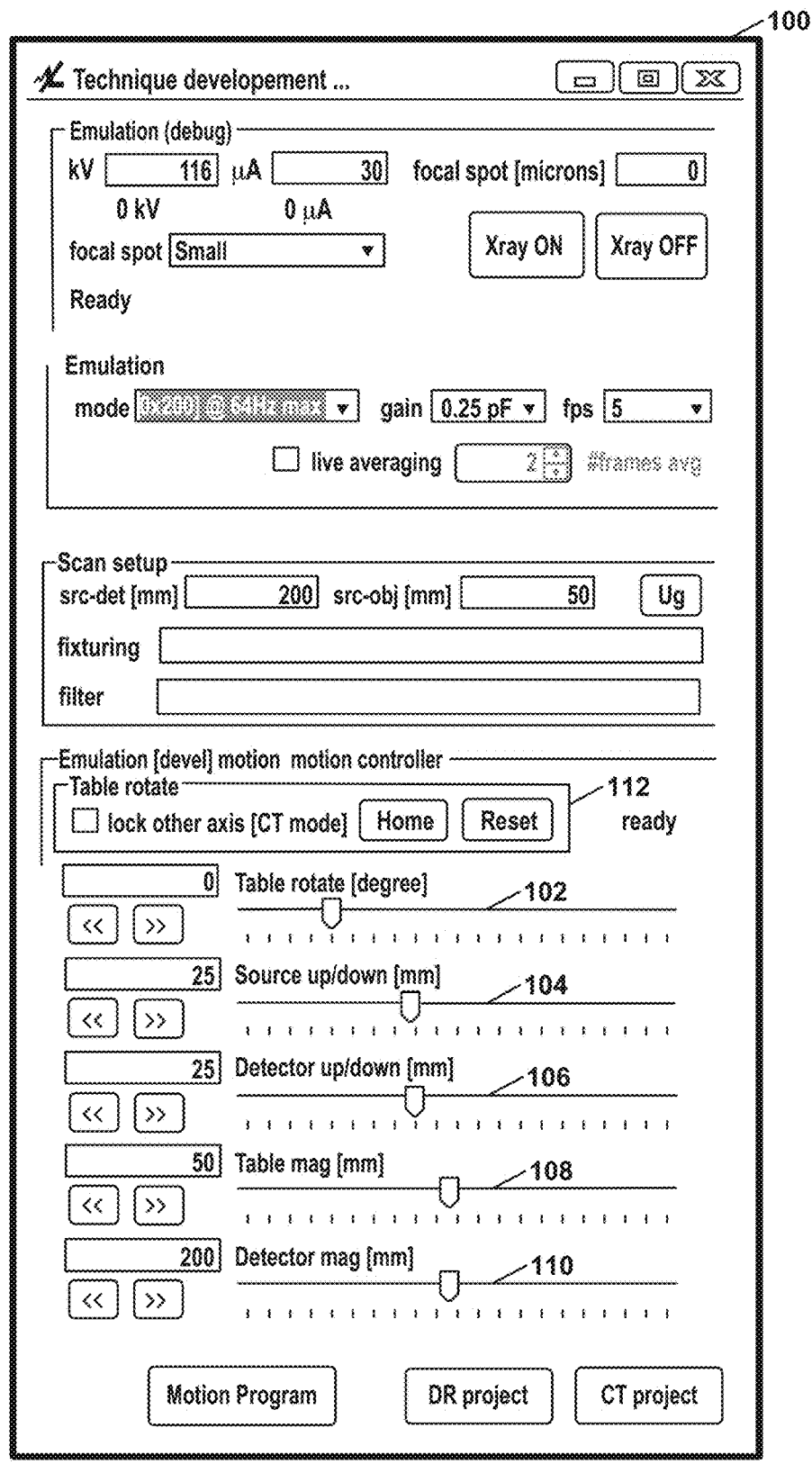
FIG. 3A is a diagram illustrating an example system parameter setup interface, in accordance with one or more techniques of this disclosure.
Figure 3B:
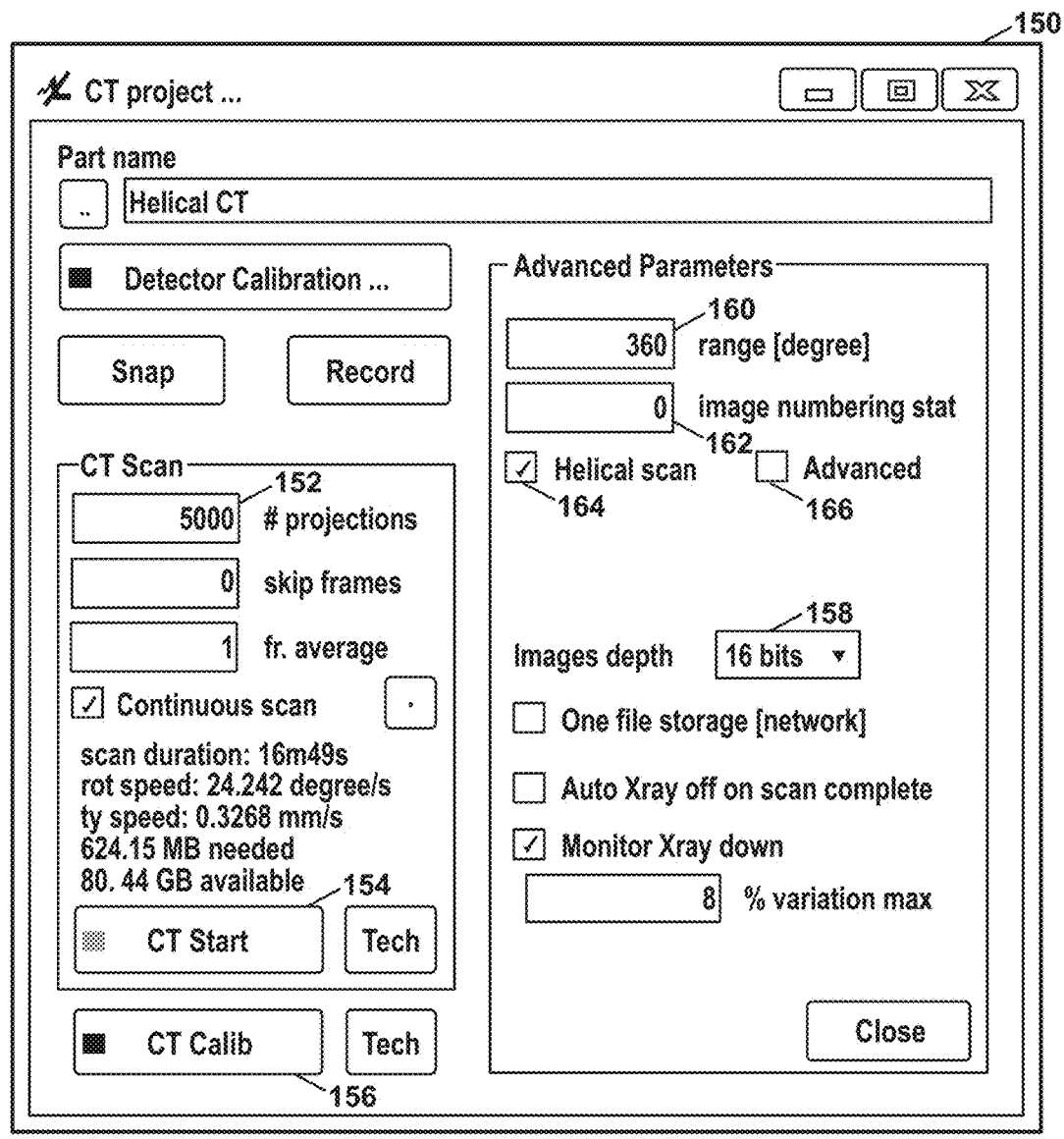
FIG. 3B is a diagram illustrating an example conventional (i.e., non-spiral) computed tomography (CT) scan setup interface, in accordance with one or more techniques of this disclosure.
Figure 3C:
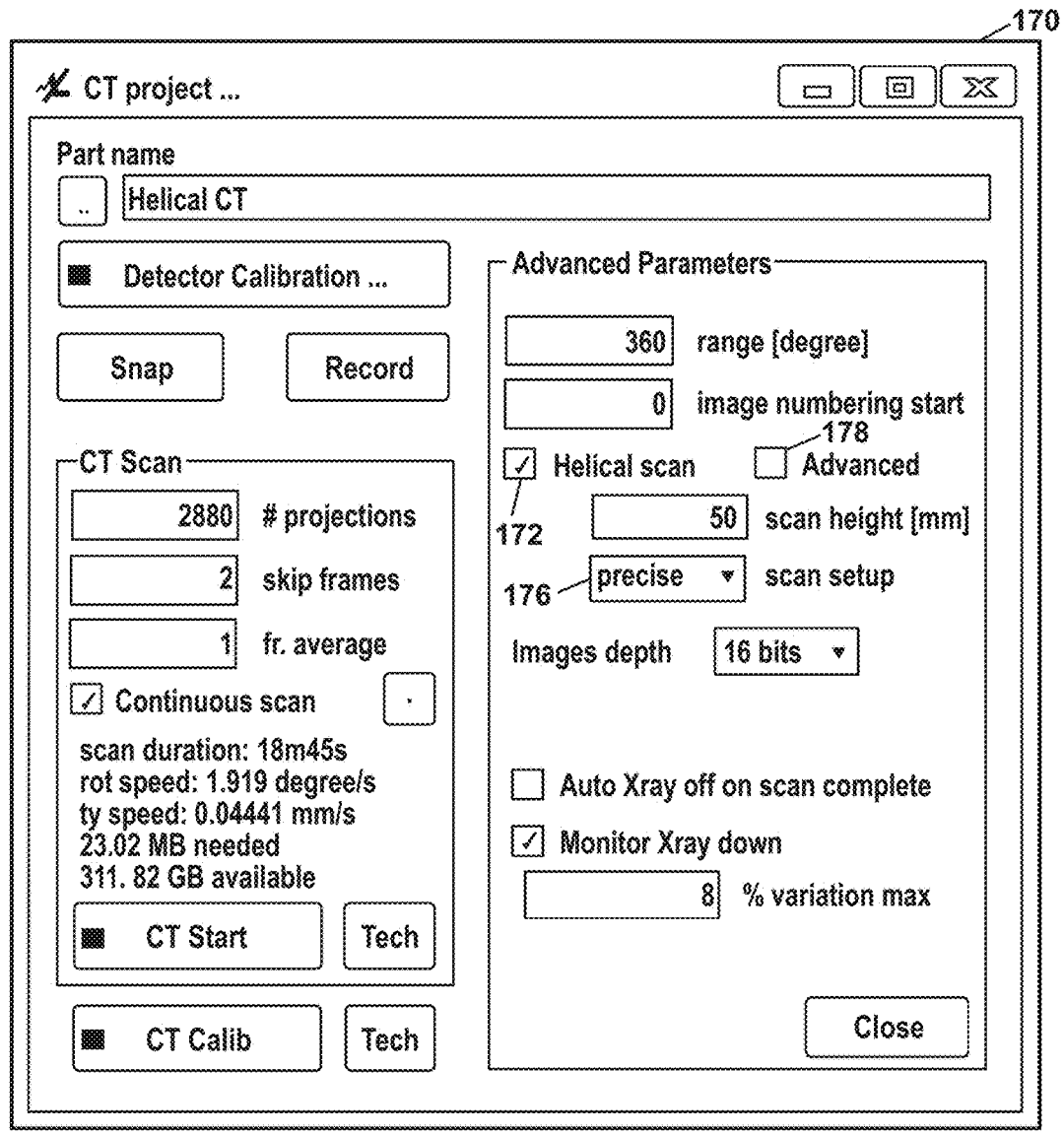
FIG. 3C is a diagram illustrating another example conventional (i.e., non-spiral) CT scan setup interface, in accordance with one or more techniques of this disclosure.
Figure 3D:
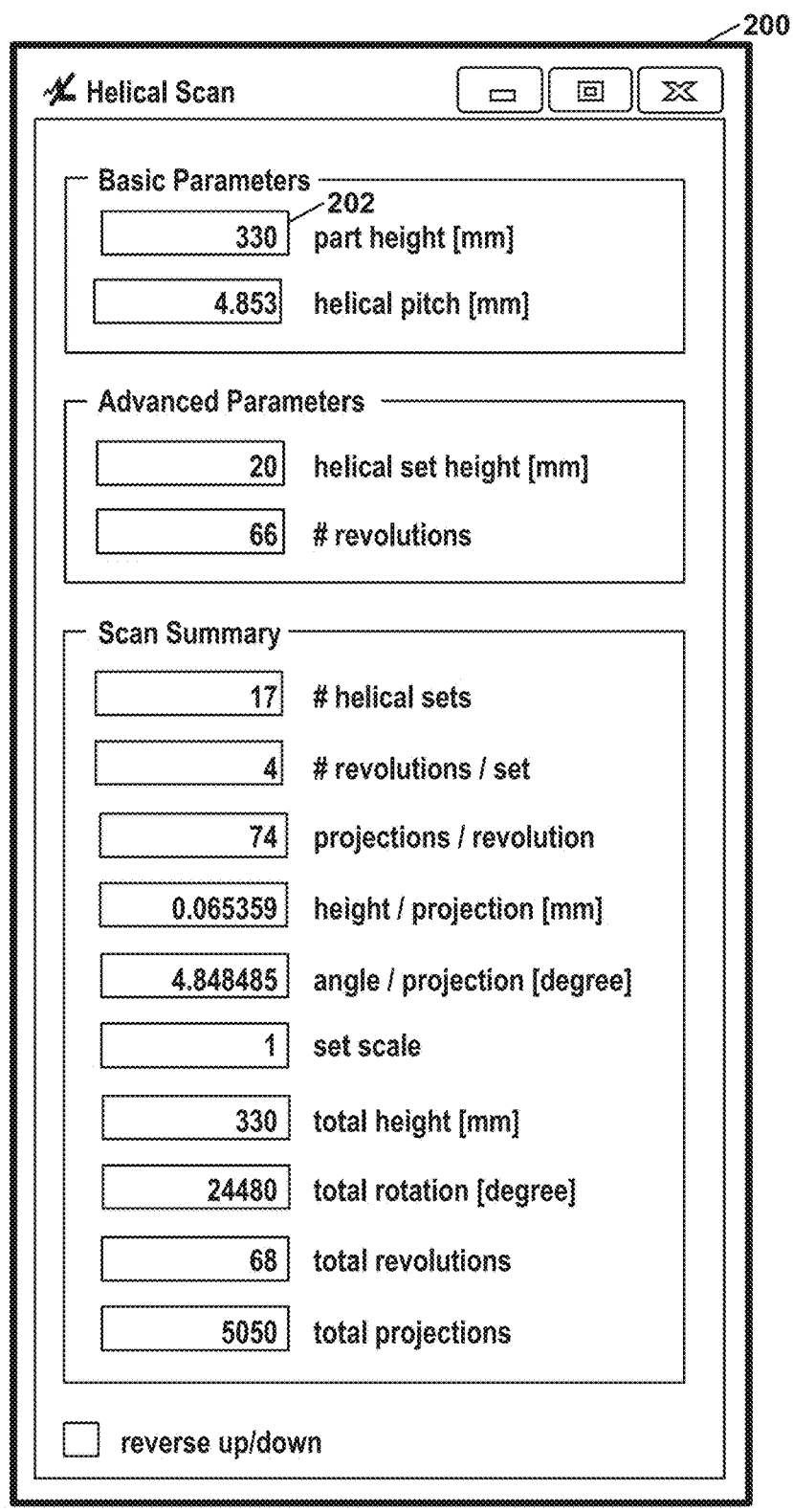
FIG. 3D is a diagram illustrating an example spiral CT scan setup interface, in accordance with one or more techniques of this disclosure.
Figure 3E:
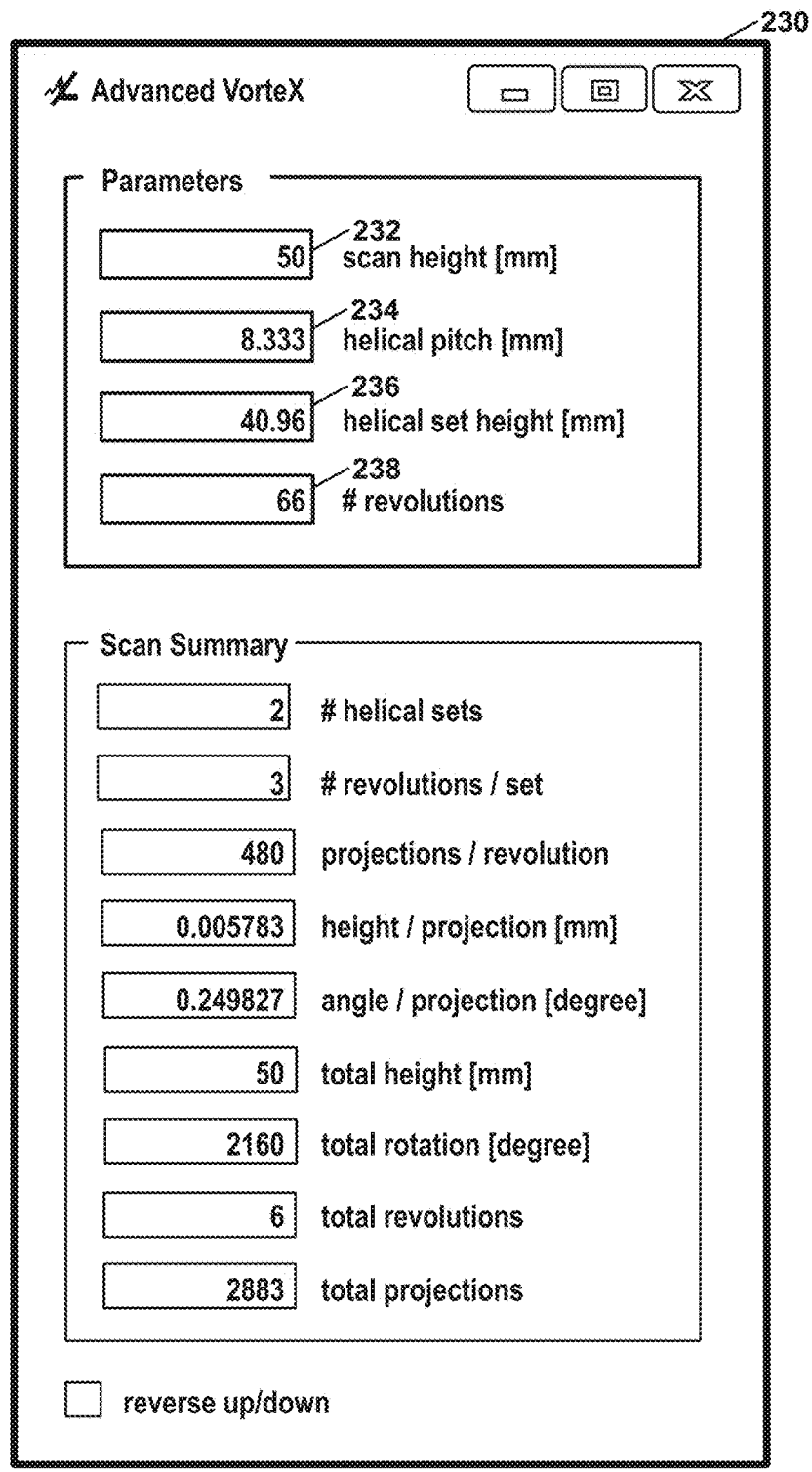
FIG. 3E is a diagram illustrating another example spiral CT scan setup interface, in accordance with one or more techniques of this disclosure.
Figure 3F:
FIG. 3F is a diagram illustrating an example image preview interface, in accordance with one or more techniques of this disclosure.

FIGS. 3A-3F are diagrams illustrating example user control interfaces for spiral-CT, in accordance with one or more techniques of this disclosure. In particular, FIG. 3A is a diagram illustrating an example system parameter setup interface 100. FIG. 3B is a diagram illustrating an example conventional (i.e., non-spiral) CT scan setup interface 150. FIG. 3C is a diagram illustrating another example conventional (i.e., non-spiral) CT scan setup interface 170, in accordance with one or more techniques of this disclosure. FIG. 3D is a diagram illustrating an example spiral CT scan setup interface 200. FIG. 3E is a diagram illustrating another example spiral CT scan setup interface 230, in accordance with one or more techniques of this disclosure. FIG. 3F is a diagram illustrating an example image preview interface 250. Particularly, image preview interface 250 illustrates an emulation environment.

System parameter setup interface 100 of FIG. 3A includes user interface (UI) elements for controlling industrial CT system 10. The UI elements of industrial CT system 10 may enable data acquisition system 26 to receive user input of parameters common to both spiral CT and non-spiral CT. For instance, system parameter setup interface 100 includes a UI element 102 for controlling table rotation (i.e., rotary stage 16), a UI element 104 for controlling a position of an x-ray source (e.g., x-ray generator 12), a UI element 106 for controlling a position of radiation detector 14, a UI element 108 for controlling a table magnification (e.g., a position of rotary stage 16 relative to x-ray generator 12 and radiation detector 14), and a UI element 110 for controlling a magnification level of radiation detector 14. Furthermore, system parameter setup interface 100 includes a set of UI elements 112 for controlling whether motion axis that are unused during a CT scan should be disabled, e.g. 108 and 110. The home UI element within system parameter setup interface 100 may drive the table rotation to a fixed reference position. The reset UI element within system parameter setup interface 100 sets the current table rotation angle to zero.

Conventional CT scan setup interface 150 of FIG. 3B may include UI elements for configuring industrial CT system 10 to perform a non-spiral CT scan. For example, conventional CT scan setup interface 150 may include a field 152 for entry of the number of projections to be captured during a CT scan. Conventional CT scan setup interface 150 may also include a UI element to skip frames (projections) to synchronize a desired x-ray detector acquisition rate with a table rotation rate that mitigates motion blur. A number of frames may be averaged together into a single projection to reduce noise using the "fr. average" UI element. Furthermore, conventional CT scan setup interface 150 may include a button 154 to initiate a CT scan and another button 156 to initiate a calibration process for industrial CT system 10. In addition, conventional CT scan setup interface 150 includes a dropdown box 158 to control the bit depth of pixels of radiographs acquired in the CT scan. Conventional CT scan setup interface 150 also includes a textbox 160 for entry of a degree range through which rotary stage 16 rotates during the CT scan. The degree range may be greater than or equal to 0. In some instances, the degree range may be greater than 360 degrees. Furthermore, conventional CT scan setup interface 150 includes a textbox 162 for entry of a number from data acquisition system 26 starts numbering radiographs acquired during the CT scan. The numbering of the radiographs may be used for subsequent reference to individual radiographs acquired during the CT scan. Conventional CT scan setup interface 150 may also provide UI elements to acquire (snap) a screenshot at the current position of the imaging system or record a series of screenshots (video) of the imaging window over a period of time.

As indicated above, FIG. 3C is a diagram illustrating another example conventional (i.e., non-spiral) CT scan setup interface 170, in accordance with one or more techniques of this disclosure. The helical scan setup interface within FIG. 3C may be displayed by selecting the checkbox 172, labeled "VorteX." The user may enter the range of linear travel in the "scan height" input field. The type of scan may be selected using a "scan setup" drop down element 176. Options in the scan setup drop down element 176 may include fast, medium, or precise, which reflect a scan duration-to-quality tradeoff. The scan setup selection may combine with the scan height to automatically choose other scan-dependent parameters. When a user enters the scan height and setup, data acquisition system 26 may receive indications of user input of the scanning parameters.

Data acquisition system 26 may output spiral CT scan setup interface 200 of FIG. 3D for display in response to receiving an indication of user input to select a helical scan checkbox 164 and/or an advanced checkbox 166 in conventional CT scan setup interface 150 or checkbox 172 and/or an advanced checkbox 178 in conventional CT scan setup interface 170. In accordance with one or more techniques of this disclosure, the user may enter a small number of scanning parameters, such as a scan range of linear translation stage 20 (i.e., linear scan range) and optionally the range of linear travel through each spiral revolution and the number of revolutions, in the advanced menu. The linear scan range parameter is indicated as "part height" in the example of FIG. 3D. When a user enters the scanning parameters, data acquisition system 26 may receive indications of user input of the scanning parameters.

Computing system 22 may execute a data acquisition control program to automatically optimize key image acquisition parameters (such as total number of projection, angular spacing, the relative rate of linear and rotation motion) based on these user inputs and other geometric parameters such as the x-ray generator spot size, detector pixel size, magnification, etc. The image acquisition parameters may also be referred to herein as "data acquisition parameters." This optimization may be performed with a set of proprietary mathematical algorithms that, for example, calculate the necessary number of projections to prevent under-sampling artefacts and accommodate the user's time budget for acquisition.

In this way, computing system 22 may use one or more algorithms to determine, based at least in part on the linear scan range, one or more additional data acquisition parameters and may configure, based at least in part on the one or more additional data acquisition parameters, industrial CT system 10 to acquire the radiographs. In one example, data acquisition system 26 may accept user input parameters, the user input parameters consisting of a linear scan range and duration-to-quality scan setup only. In this example, data acquisition system 26 uses algorithms to determine additional data acquisition parameters, such as the number of projections, frames to skip, helical pitch and number of revolutions.

As the spiral CT input is more complex and some key input parameters may be less intuitive than conventional CT setups, having such an optimization system to reduce the user's effort may be helpful to making this technique practical, particularly for a multi-scale x-ray imaging system spanning a wide resolution and field of view range.

For instance, in the example of FIG. 3D, data acquisition system 26 may receive an indication of user input of a part height in field 202. The part height may indicate a height (or length) of a part (e.g., sample) under test. In response, data acquisition system 26 may calculate, based at least in part on the part height, other values shown in spiral CT scan setup interface 200, such as a helical pitch, a number of helical sets, a number of revolutions per set, a number of projections per revolution, height difference per projection, angle difference per projection, a set scale indicating the filtered weight to apply per helical set, total height difference in the CT scan, total number of degrees rotated in the CT scan, the total number of revolutions of the sample during the CT scan, and the total number of projections (e.g., radiographs) acquired during the CT scan. Data acquisition system 26 may receive indications of user input of the helical set height and a number of revolutions during the CT scan and may cause data acquisition system 26 to update its parameter calculations. A helical set comprises a number of consecutive revolutions in the helix whose projected radiographs have, for example, 50% overlap vertically. The helical set height is the vertical extent of a helical set. When a user enters the scanning parameters, data acquisition system 26 may receive indications of user input of the scanning parameters. Data acquisition system 26 may use values entered in conventional CT scan setup interface 150 in addition to values entered in spiral CT scan setup interface 200 to calculate the scan summary parameters shown in FIG. 3D. In this way, the user does not need to manually calculate or input these parameters; rather the scan summary parameters are computed, such as total projections from the scan height and height per projection.

As indicated above, FIG. 3E is a diagram illustrating another example spiral CT scan setup interface 230, in accordance with one or more techniques of this disclosure. Spiral CT scan setup interface 230 is similar in some respects to spiral CT scan setup interface 200 of FIG. 3D, but includes a number of different features.

Data acquisition system 26 may output spiral CT scan setup interface 230 of FIG. 3E for display in response to receiving an indication of user input to select a helical scan advanced checkbox 166 in conventional CT scan setup interface 150 or checkbox 172 and/or an advanced checkbox 178 in conventional CT scan setup interface 170. In accordance with one or more techniques of this disclosure, the user may enter a small number of scanning parameters, such as a scan range of the linear stage (i.e., linear scan range), a helical set height 236, and a number of revolutions 238, in the advanced dialog. The linear scan range parameter is indicated as a "scan height" element 232 in the example of FIG. 3E. Output scan setup interface 200 also indicates a helical pitch parameter 234.

In the example of FIG. 3E, data acquisition system 26 may calculate, based at least in part on the scan height, helical pitch, helical set height, and/or number of revolutions, a number of helical sets, a number of revolutions per set, a number of projections per revolution, a height difference per projection, an angle difference per projection, a total height difference in the CT scan, a total number of degrees rotated in the CT scan, a total number of revolutions of the sample during the CT scan, and a total number of projections (e.g., radiographs) acquired during the CT scan.

FIGS. 4A-4E illustrate example images of a test structure scanned using a spiral-CT technique and a conventional CT technique, in accordance with one or more techniques of this disclosure. Using a flat-panel detector, the data was acquired using the parameters optimized with an algorithm as described above. The conventional CT image shows only a small region of the entire structure. In order to obtain the complete structure, a number of such scans may be performed and numerically stitched in post-processing. In contrast, the spiral-CT image was acquired in a single cycle. The spiral-CT data also shows better contrast and resolution with fewer artifacts than conventional CT.

Figure 4A:
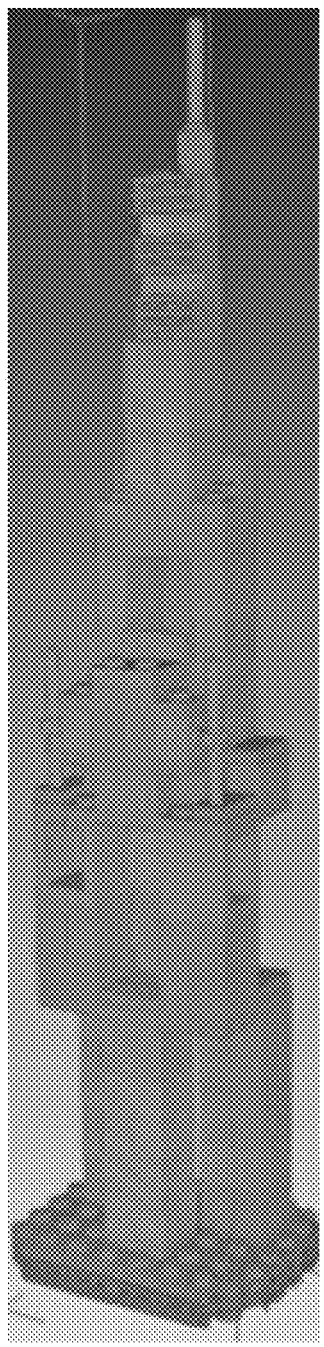
FIG. 4A is a diagram illustrating a volume rendering of an example 3-dimensional structure obtained using spiral-CT.
Figure 4B:
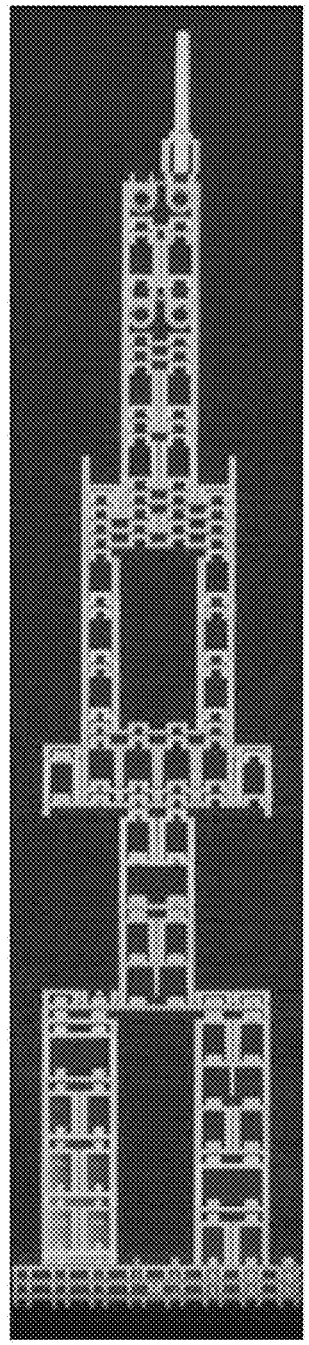
FIG. 4B is a diagram illustrating a first example cross-sectional image of the 3-dimensional structure of FIG. 4A.
Figure 4C:
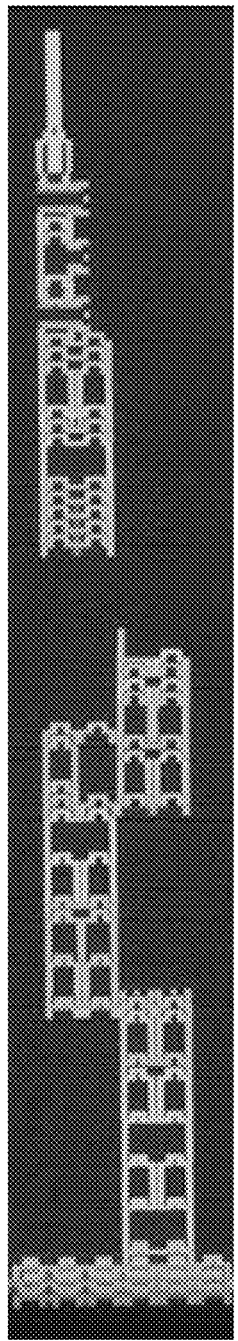
FIG. 4C is a diagram illustrating a second example cross-sectional image of the 3-dimensional structure of FIG. 4A.
Figure 4D:
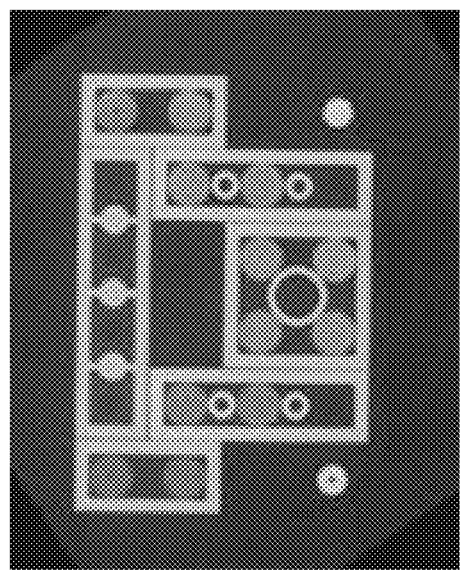
FIG. 4D is a diagram illustrating a third example cross-sectional image of the 3-dimensional structure of FIG. 4A.

FIG. 4A is a diagram illustrating a volume rendering of an example 3-dimensional structure obtained using spiral-CT. FIG. 4B is a diagram illustrating a first example cross-sectional image of the 3-dimensional structure of FIG. 4A. FIG. 4C is a diagram illustrating a second example cross-sectional image of the 3-dimensional structure of FIG. 4A. FIG. 4D is a diagram illustrating a third example cross-sectional image of the 3-dimensional structure of FIG. 4A. In other words, the 3D structure obtained using spiral-CT is shown in FIG. 4A as a volume rendering, and its cross-sectional images are shown in FIGS. 4B, 4C, and 4D along the three axes.

Figure 4E:
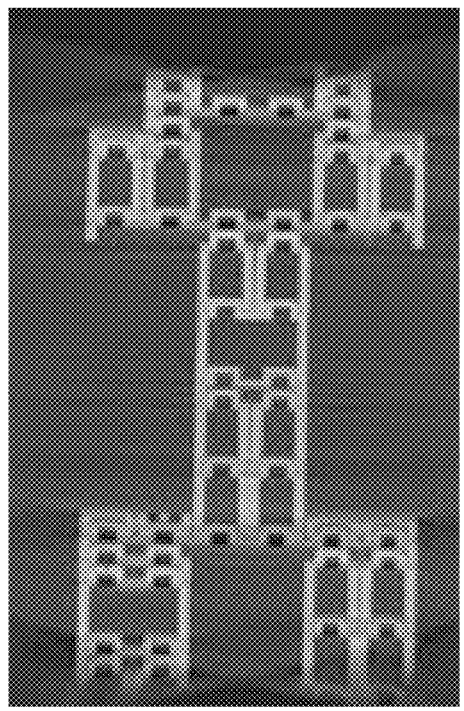
FIG. 4E is a diagram illustrating an example cross-sectional image of the 3-dimensional structure of FIG. 4A.

FIG. 4E is a diagram illustrating an example cross-sectional image of the 3-dimensional structure of FIG. 4A. In other words, for comparison, the result from conventional volumetric CT is shown in FIG. 4E. The artifacts in conventional CT images are most prominent at the top and bottom of reconstruction area shown in FIG. 4E where the images are exposed to x-rays at high cone angles. Such artifacts may be particularly common for structures containing primarily flat structures aligned perpendicular to the rotation axis. Whereas these exposure angles are fixed during a conventional CT scan, they may vary in a spiral scan sequence as linear translation stage 20 translates. As a consequence, the influence of these high-angle artifacts can be reduced or eliminated by filtering projection radiographs. Accordingly, one or more processors of data acquisition system 26 (FIG. 1) may be configured to perform digital filtering calculations with acquired radiographs to reduce artifacts associated with particular cone angles (e.g., high cone angles) of the x-ray beam. Several possible filters can be used depending on the sample type.

Figure 5:
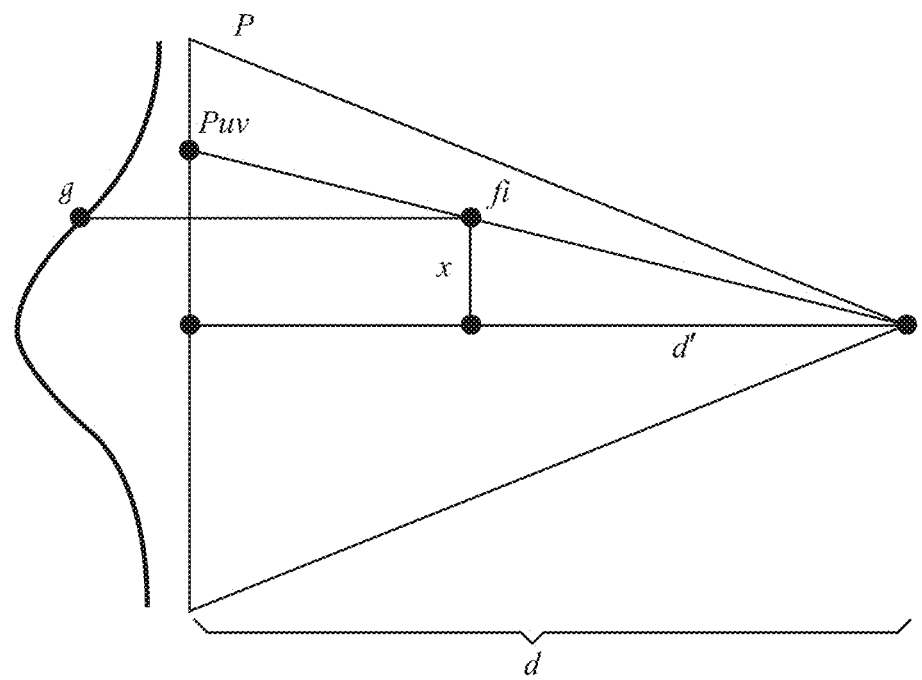
FIG. 5 is a conceptual illustration of a weighted back-projection functional construction, in accordance with one or more techniques of this disclosure.

For example, one or more processors of data acquisition system 26 may be configured to perform digital filtering calculations including a Gaussian-type digital filter with acquired radiographs. In other words, data acquisition system 26 may use a Gaussian-type digital filter to filter each of the radiographs. In this example, a weighted back-projection filtering function, such as a Gaussian-type function $f_i = \Sigma_{n=1}^{N} g_n \cdot k_n^2 \cdot p_{nuv}$, may be used to give greater weight to low-angle slices in a smoothly varying fashion, where, $$g = \exp\left[-\frac{x^2}{2\sigma^2}\right],$$

and $$k = \frac{d}{d'}$$

as indicated in the example of FIG. 5. Thus, FIG. 5 is a conceptual illustration of a weighted back-projection functional construction, in accordance with one or more techniques of this disclosure.

In another example, data acquisition system 26 may use a step function digital filter to filter each of the acquired radiographs. A step function may make sharp cut offs at specific angles. Thus, one or more processors of data acquisition system 26 may be configured to perform digital filtering calculations including a step function digital filter.

Figure 6:
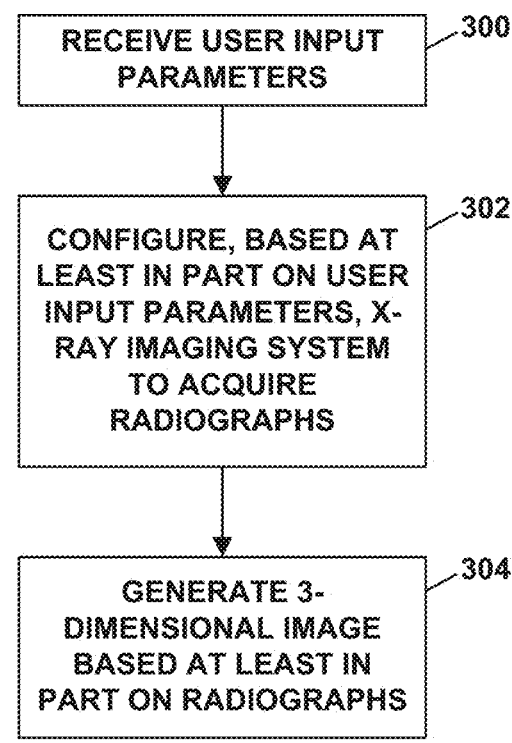
FIG. 6 is a flowchart illustrating an example operation of an industrial CT system, in accordance with one or more techniques of this disclosure.

FIG. 6 is a flowchart illustrating an example operation of industrial CT system 10, in accordance with one or more techniques of this disclosure. The example operation of FIG. 6 is explained with reference to industrial CT system 10 of FIG. 1. However, the technique shown in FIG. 6 is not necessarily limited to use in the system of FIG. 1 and may be used in other systems.

In the example of FIG. 6, a data acquisition system (e.g., data acquisition system 26) may receive user input parameters (300). In other words, data acquisition system 26 may receive an indication of user input of the user input parameters. In some examples, data acquisition system 26 may receive user input of a linear scan range. The linear scan range may be a range of linear motion of a linear translation stage (e.g., linear translation stage 20). Furthermore, in this example, data acquisition system 26 may use one or more algorithms to determine, based at least in part on the linear scan range, one or more additional data acquisition parameters.

The data acquisition system may configure, based at least in part on the user input parameters, an x-ray imaging system (e.g., industrial CT system 10) to acquire radiographs (302). As described elsewhere in this disclosure, an x-ray imaging system may comprise an x-ray generator (e.g., x-ray generator 12), one or more radiation detectors (e.g., radiation detector 14), a rotary stage (e.g., rotary stage 16) having an axis of rotation (e.g., axis of rotation 17) arranged perpendicular to an axis of x-ray beam 18 emitted by x-ray generator 12, and a linear translation stage 20 having an axis arranged along the axis of rotation 17 of rotary stage 16. Furthermore, the x-ray imaging system may comprise a motion control system (e.g., motion control system 24) that synchronizes rotational motion of rotary stage 16 and linear motion of linear translation stage 20. Data acquisition system 26 may generate a three-dimensional image based at least in part on the radiographs (304).

The following paragraphs provide further examples of this disclosure.

Example 1

An x-ray imaging system comprising: an x-ray generator; one or more radiation detectors; a rotary stage having an axis of rotation arranged substantially perpendicular to an axis of an x-ray beam emitted by the x-ray generator; a linear translation stage having an axis arranged along the axis of rotation of the rotary stage; a motion control system that synchronizes rotational motion of the rotary stage and linear motion of the linear translation stage; and a data acquisition system comprising one or more processors configured to: receive user input parameters; configure, based at least in part on the user input parameters, the x-ray imaging system to acquire radiographs; and generate a three-dimensional image based at least in part on the radiographs.

Example 2

The x-ray imaging system of example 1, wherein the one or more radiation detectors include a flat-panel radiation detector.

Example 3

The x-ray imaging system of examples 1 or 2, wherein the one or more processors of the data acquisition system are further configured to perform digital filtering calculations with the radiographs.

Example 4

The x-ray imaging system of example 3, wherein the digital filter calculations include a Gaussian-type digital filter.

Example 5

The x-ray imaging system of example 3 or 4, wherein the digital filter calculations include a step function digital filter.

Example 6

The x-ray imaging system of any of examples 1-5, wherein the x-ray generator provides x-rays with an energy range of 20 keV to 600 keV.

Example 7

The x-ray imaging system of any of examples 1-6, wherein the one or more radiation detectors include a lens-coupled high-resolution x-ray detector.

Example 8

The x-ray imaging system of example 7, wherein the lens-coupled high-resolution x-ray detector has a pixel size in a range of 0.1 micrometers to 10 micrometers.

Example 9

The x-ray imaging system of example 8, wherein the one or more radiation detectors include a flat-panel detector with a pixel size ranging from 25 micrometers to 300 micrometers.

Example 10

The x-ray imaging system of examples 7 or 8, wherein the one or more radiation detectors include a flat-panel detector and the x-ray imaging system further comprises a mechanical mechanism to switch between at least the lens-coupled high-resolution x-ray detector and the flat-panel detector.

Example 11

The x-ray imaging system of any of examples 1-10, wherein the one or more radiation detectors include a linear diode array type radiation detector.

Example 12

The x-ray imaging system of any of examples 1-11, wherein the user input parameters consist of a linear scan range and the one or more processors of the data acquisition system are configured to: use one or more algorithms to determine, based at least in part on the linear scan range, one or more additional data acquisition parameters; and configure, based at least in part on the one or more additional data acquisition parameters, the x-ray imaging system to acquire the radiographs.

Example 13

The method of example 12, wherein the one or more algorithms to determine the additional data acquisition parameters include one or more embedded algorithms.

Example 14

The x-ray imaging system of any of examples 1-13, wherein the data acquisition system is computer-controlled.

Example 15

The x-ray imaging system of any of examples 1-14, wherein the one or more processors of the data acquisition system are configured to digitally record the radiographs.

Example 16

An x-ray imaging system configured according to any of examples 1-15.

Example 17

An x-ray imaging system according to any of technique disclosed herein.

Example 18

An x-ray imaging system comprising: an x-ray generator; one or more radiation detectors including flat-panel radiation detectors, lens-coupled high-resolution x-ray detectors, and linear diode arrays; a rotary stage with an axis arranged perpendicular to an x-ray beam axis; a linear translation stage with an axis arranged along the axis of the rotary stage; a motion control system configured to synchronize the motion of rotary stage and the linear translation stage; and a computer-controlled data acquisition system that accepts user input parameters, acquires radiographs, digitally records radiographs, performs digital filtering calculations with the radiographs, and executes computer code to reconstruct a three-dimensional image from the radiographs.

Example 19

The x-ray imaging system of example 18, wherein the x-ray generator provides x-rays with energy range of 20 keV to 600 keV.

Example 20

The x-ray imaging system of examples 18 or 19, comprising a lens-coupled high-resolution detector with a pixel size in a range of 0.1 micrometers to 10 micrometers.

Example 21

The x-ray imaging system of any of examples 18-20, comprising a linear diode array type radiation detector.

Example 22

The x-ray imaging system of any of examples 18-21, comprising a lens-coupled high-resolution detector with a pixel size in a range of 0.1 micrometers to 10 micrometers, and a flat-panel detector with a pixel size ranging from 25 micrometers to 300 micrometers, and a mechanical mechanism to switch between the lens-coupled high-resolution detector and the flat-panel detector.

Example 23

The x-ray imaging system of any of examples 18-22, wherein the user input parameters consists of a linear scan range only and uses embedded algorithms to determine additional data acquisition parameters.

Example 24

The x-ray imaging system of any of examples 18-23 wherein a Gaussian type digital filter is used to process each radiograph.

Example 25

The x-ray imaging system of any of examples 18-24, wherein a step function digital filter is used to process each radiograph.

Example 26

An x-ray imaging system configured according to any of examples 18-25.

The techniques of this disclosure may be implemented in a wide variety of devices or apparatuses. Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

In one or more examples, particular functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, particular portions of the techniques may be implemented in one or more circuits or logic elements.

Various examples have been described. These and other examples are within the scope of the following claims.

What is claimed is:
1. An x-ray imaging system comprising:
an x-ray generator;
a radiation detector;

a rotary stage having an axis of rotation arranged perpendicular to an axis of an x-ray beam emitted by the x-ray generator;
a linear translation stage having an axis of movement arranged along the axis of rotation of the rotary stage;
a motion control system that synchronizes rotational motion of the rotary stage and linear motion of the linear translation stage; and
a data acquisition system comprising one or more processors configured to:
output a user interface (UI);
receive a plurality of user input parameters via the user interface, the plurality of user input parameters including a linear scan range, a helical pitch, and a helical set height, the linear scan range indicating a height of an object;
determine, based at least in part on the linear scan range, the helical pitch, and/or the helical set height, a total number of helical sets to be performed during a spiral computed tomography (CT) scan, each of the helical sets being a number of consecutive revolutions in a helix whose projected radiographs have a given percentage of vertical overlap;
configure, based at least in part on the plurality of user input parameters, the data acquisition system to acquire radiographs from the radiation detector during the spiral CT scan; and
generate a three-dimensional image of the object based at least in part on the radiographs, the object being on the rotary stage.

2. The x-ray imaging system of claim 1, wherein the radiation detector includes a flat-panel detector.

3. The x-ray imaging system of claim 1, wherein the x-ray generator provides x-rays with an energy range of 20 keV to 600 keV.

4. The x-ray imaging system of claim 1, wherein the radiation detector includes a lens-coupled high-resolution x-ray detector.

5. The x-ray imaging system of claim 4, wherein the lens-coupled high-resolution x-ray detector has a pixel size in a range of 0.1 micrometers to 10 micrometers.

6. The x-ray imaging system of claim 5, wherein the radiation detector further includes a flat-panel detector with a pixel size ranging from 25 micrometers to 300 micrometers.

7. The x-ray imaging system of claim 4, wherein the radiation detector further includes a flat-panel detector, and the lens-coupled high-resolution x-ray detector and the flat-panel detector are switchable in the x-ray imaging system.

8. The x-ray imaging system of claim 1, wherein the radiation detector includes a linear diode array detector.

9. The x-ray imaging system of claim 1, wherein:
the data acquisition system is further configured to calculate, based at least in part on the linear scan range, another user input parameter in the plurality of user input parameters,
wherein the other user input parameter is one of: a number of revolutions per set, a number of projections per revolution, a height difference per projection, an angle difference per projection, a total height difference in the spiral CT scan, a total number of degrees rotated in the spiral CT scan, or a total number of projections acquired during the spiral CT scan.

10. A method comprising:
outputting a user interface (UI);
receiving a plurality of user input parameters via the user interface, the plurality of user input parameters including a linear scan range, a helical pitch, and a helical set height, the linear scan range indicating a height of an object;
determining, based at least in part on the linear scan range, the helical pitch, and/or the helical set height, a total number of helical sets to be performed during a spiral computed tomography (CT) scan, each of the helical sets being a number of consecutive revolutions in a helix whose projected radiographs have a given percentage of vertical overlap;
configuring, based at least in part on the plurality of user input parameters, an x-ray imaging system to acquire radiographs during the spiral CT scan, the x-ray imaging system comprising:
an x-ray generator;
a radiation detector;
a rotary stage having an axis of rotation arranged perpendicular to an axis of an x-ray beam emitted by the x-ray generator;
a linear translation stage having an axis of movement arranged along the axis of rotation of the rotary stage; and
a motion control system that synchronizes rotational motion of the rotary stage and linear motion of the linear translation stage; and
generating a three-dimensional image of the object based at least in part on the radiographs, the object being on the rotary stage.

11. The method of any of claim 10, wherein the x-ray generator provides x-rays with an energy range of 20 keV to 600 keV.

12. The method of claim 10, wherein the radiation detector includes a lens-coupled high-resolution x-ray detector.

13. The method of claim 12, wherein the lens-coupled high-resolution x-ray detector has a pixel size in a range of 0.1 micrometers to 10 micrometers.

14. The method of claim 13, wherein the radiation detector further includes a flat-panel detector with a pixel size ranging from 25 micrometers to 300 micrometers.

15. The method of claim 12, wherein the radiation detector further includes a flat-panel detector, the lens-coupled high-resolution x-ray detector and the flat-panel detector are switchable in the x-ray imaging system.

16. The method of claim 10, wherein the radiation detector includes a linear diode array detector.

17. The method of claim 10, wherein:
the method further comprises calculating, based at least in part on the linear scan range, another user input parameter in the plurality of user input parameters,
wherein the other user input parameter is one of: a number of revolutions per set, a number of projections per revolution, a height difference per projection, an angle difference per projection, a total height difference in the spiral CT scan, a total number of degrees rotated in the spiral CT scan, or a total number of projections acquired during the spiral CT scan.

18. A non-transitory computer-readable data storage medium having instructions stored thereon that, when executed, cause a computing system to:
output a user interface (UI);
receive a plurality of user input parameters via the user interface, the plurality of user input parameters including a linear scan range, a helical pitch, and a helical set height, the linear scan range indicating a height of an object;

determine, based at least in part on the linear scan range, the helical pitch, and/or the helical set height, a total number of helical sets to be performed during a spiral computed tomography (CT) scan, each of the helical sets being a number of consecutive revolutions in a helix whose projected radiographs have a given percentage of vertical overlap;

configure, based at least in part on the plurality of user input parameters, an x-ray imaging system to acquire radiographs during the spiral CT scan, the x-ray imaging system comprising:

an x-ray generator;

a radiation detector;

a rotary stage having an axis of rotation arranged perpendicular to an axis of an x-ray beam emitted by the x-ray generator;

a linear translation stage having an axis of movement arranged along the axis of rotation of the rotary stage; and a motion control system that synchronizes rotational motion of the rotary stage and linear motion of the linear translation stage such that a point on a sample supported by the rotary stage traces out a spiral or helical pattern; and generate a three-dimensional image of the object based at least in part on the radiographs, the object being on the rotary stage.

* * * * *